US00PP11872P2

(12) United States Plant Patent
Fruehwirth

(10) Patent No.: US PP11,872 P2
(45) Date of Patent: May 15, 2001

(54) POINSETTIA PLANT NAMED 'ECKABBO'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/427,729

(22) Filed: Oct. 27, 1999

(51) Int. Cl.[7] ..... A01H 5/00
(52) U.S. Cl. ..... Plt./307

(58) Field of Search ..... Plt./303, 306, 307

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Poinsettia plant named 'Eckabbo', characterized by its smooth crimson red bracts that are held horizontally; response time 9 weeks; freely flowering habit; very dark green leaves with red purple petioles; upright plant habit; freely branching habit; and excellent postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckabbo'.

The new cultivar is a product of a planned breeding program conducted by the Inventor in Encinitas, Calif. The objective of the program is to create new Poinsettia cultivars having interesting bract and leaf display, color and form; strong and freely branching stems; and good post-production longevity.

The new cultivar originated from a cross made by the Inventor of the proprietary selection identified as H-43, as the female, or seed parent with the proprietary selection identified as F-14, as the male, or pollen parent.

The cultivar 'Eckabbo' was discovered and selected by the Inventor as a flowering plant within the progeny of the stated cross in a controlled environment in Encinitas, Calif. in December, 1995.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckabbo'. These characteristics in combination distinguish 'Eckabbo' as a new and distinct cultivar:

1. Smooth crimson red bracts that are held horizontally.
2. Response time about 9 weeks.
3. Freely flowering.
4. Very dark green leaves with red purple petioles.
5. Upright plant habit.
6. Freely branching habit.
7. Excellent postproduction longevity.

In side-by-side comparsions conducted in Encinitas, Calif., plants of the new Poinsettia have a darker leaf and bract color than plants of the female parent, the selection H-43. Compared to plants of the male parent, the selection F-14, plants of the new Poinsettia have more upright and darker-colored bracts.

Plants of the new Poinsettia can be compared to plants of the cultivar '490', disclosed in U.S. Plant Pat. No. 7,825. However, in side-by-side comparisons conducted in Encinitas, Calif. plants of the Poinsettia differed from plants of '490' in the following characteristics:

1. Plants of the new Poinsettia are taller, more vigorous and more upright than plants of '490'.
2. Leaves of the new Poinsettia are slightly larger and darker green than leaves of '490'.
3. Plants of the new Poinsettia flower about 7 to 10 days later than plants of '490'.
4. Inflorescences of the new Poinsettia are larger and flatter than inflorescences of '490'.
5. Flower bract color of the new Poinsettia is slightly more crimson than flower bract color of '490'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Eckabbo'.

The photograph at the bottom of the first sheet comprises a top perspective view of a typical plant of 'Eckabbo'.

The photograph on the second sheet is a close-up view of typical bracts and leaves of 'Eckabbo', (left) and '490' (right). Bract and foliage colors in the photographs may differ from actual colors due to light reflectance.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures ranging from 21 to 27° C., night temperatures ranging from 18 to 20° C., and light levels about 4,000 foot-candles. Plants were grown in 16-cm pots, pinched one time, and flowered under naturally lengthening nyctoperiods during the fall/early winter. Plants were about 17 weeks old after planting from an unrooted cutting.

In the following description, color references are made to The Royal Horticultural Society Colour Chart except where general terms of ordinary dictionary signficance are used.

Botanical classification: *Euphorbia pulcherrima* Willd. 'Eckabbo'.

Parentage:

*Female parent.*—Proprietary selection of *Euphorbia pulcherrima* Willd. identified as H-43.

*Male parent.*—Proprietary selection of *Euphorbia pulcherrima* Willd. identified as F-14.

Propagation:

*Type cutting.*—Terminal cuttings.

*Time to initiate roots.*—Summer: About 7 days at 24° C. Winter: About 10 days at 22° C.

*Time to develop roots.*—Summer : About 26 days at 24° C. Winter: About 26 days at 22° C.

*Root description.*—Freely branching, becoming fibrous with development.

Plant description:

*Plant form.*—Inverted triangle.

*Growth habit.*—Upright. Freely branching. Branching is enhanced by removing the shoot apex. Vigorous.

*Plant height.*—About 34 cm.

*Crop time.*—From unrooted cuttings to a flowering plant in a 16-cm container, about 17 weeks are required.

*Stem description.*—Number of lateral branches: About six lateral branches are formed after removal of the terminal apex. Lateral branch length: About 24.5 cm. Internode length: About 2.25 cm. Stem color: 146A; occasional red purple anthocyanin.

*Foliage description.*—Quantity of leaves per lateral branch: About 12. Length: About 14 cm. Width: About 9 cm. Shape: Ovate to lobed. Apex: Acuminate. Base: Acute. Margin: Entire. Texture: Smooth, dull; very sparse pubescence on lower surface. Color: Young foliage, upper surface: Darker than 139A. Young foliage, lower surface: 137A. Mature foliage, upper surface: Much darker than 139A. Mature foliage, lower surface: Slightly more gray than 137A. Venation, upper surface: 139D. Venation, lower surface: 139D. Petiole: Length: About 5.3 cm. Diameter: About 3 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Response time is about 9 weeks.

*Quantity of inflorescences.*—One per lateral branch, usually about six per plant.

*Inflorescence size.*—Diameter: About 32 cm. Height (depth): About 3.75 cm.

*Flower bracts.*—Quantity of flower bracts per inflorescence: Usually about 10 primary bracts and about 6 smaller secondary bracts per inflorescence. Length, largest bracts: About 14.5 cm. Width, largest bracts: About 9.5 cm. Shape: Ovate to lobed. Apex: Acuminate. Base: Acute. Margin: Entire. Texture: Smooth. Aspect: Held mostly horizontal. Color: Developing, upper surface: 46A. Developing, lower surface: 45A. Mature, upper surface: Slightly darker than 45A; fading to more rose than 53B. Mature, lower surface: 53B.

*Cyathia.*—Quantity: Usually about 13 per corymb. Diameter of cyathia cluster: About 1.5 by 2 cm. Length: About 9 mm. Width: About 5 mm. Color: Immature: 144A. Mature: 144A to 144B. Peduncle: Length: About 5 mm. Aspect: Strong, erect. Color: 144B. Stamens: Stamen number: Five to ten with numerous stamenoids per cyathium. Anther length: About 1 mm. Anther shape: Oval. Anther color: 45A. Amount of pollen: Scarce. Pollen color: 7A. Pistils: None. Nectaries: Nectary quantity: One per cyathium. Nectary color: 144A to 14A.

Disease resistance: Plants of the new Poinsettia have been observed to be resistant to Botrytis.

Postproduction longevity: Excellent; generally plants maintain good substance and bract color for about eight weeks under interior conditions.

It is claimed:

1. A new and distinct cultivar of Poinsettia plant named 'Eckabbo', as illustrated and described.

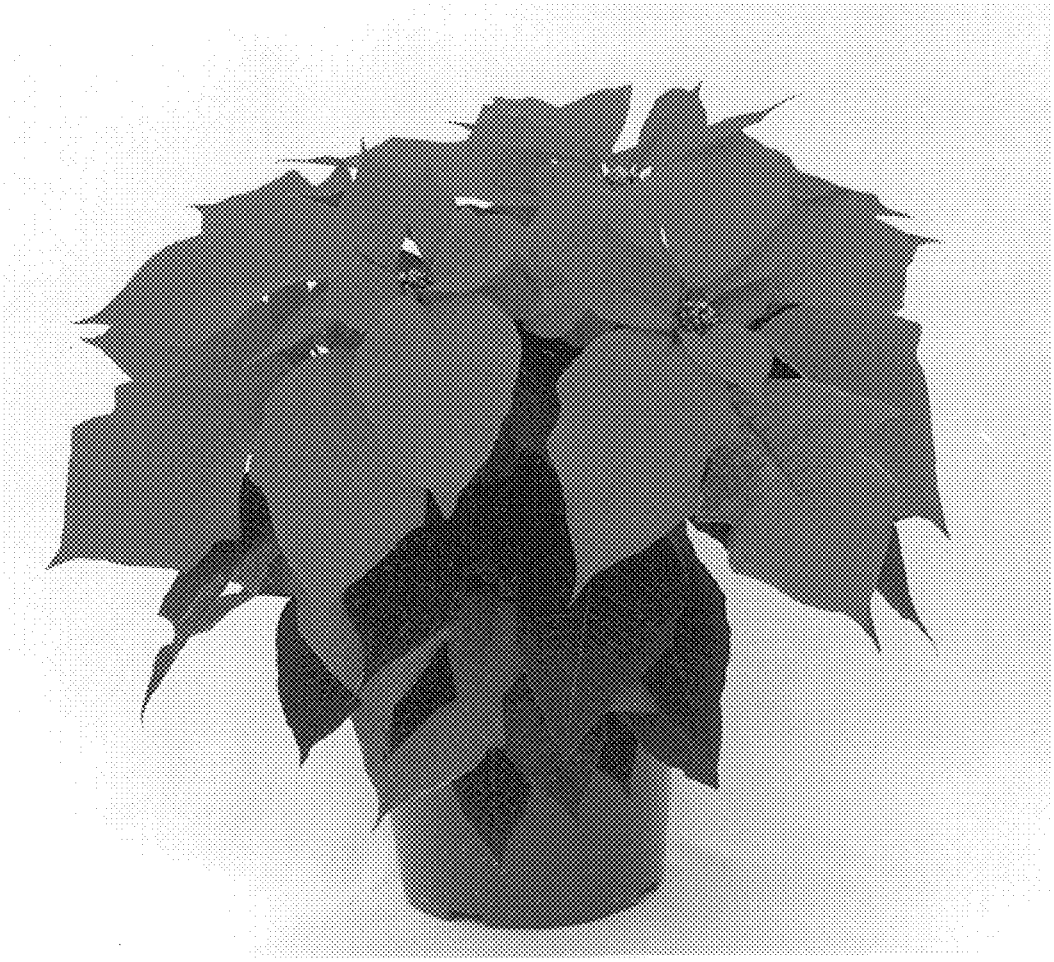
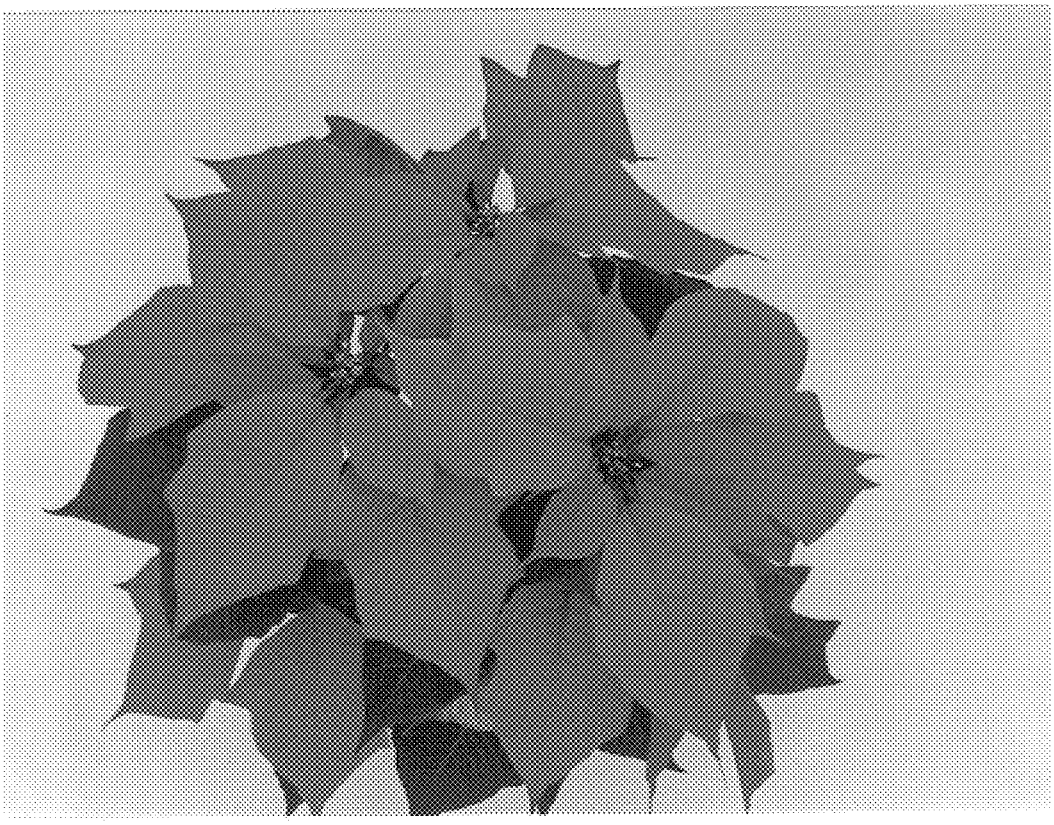

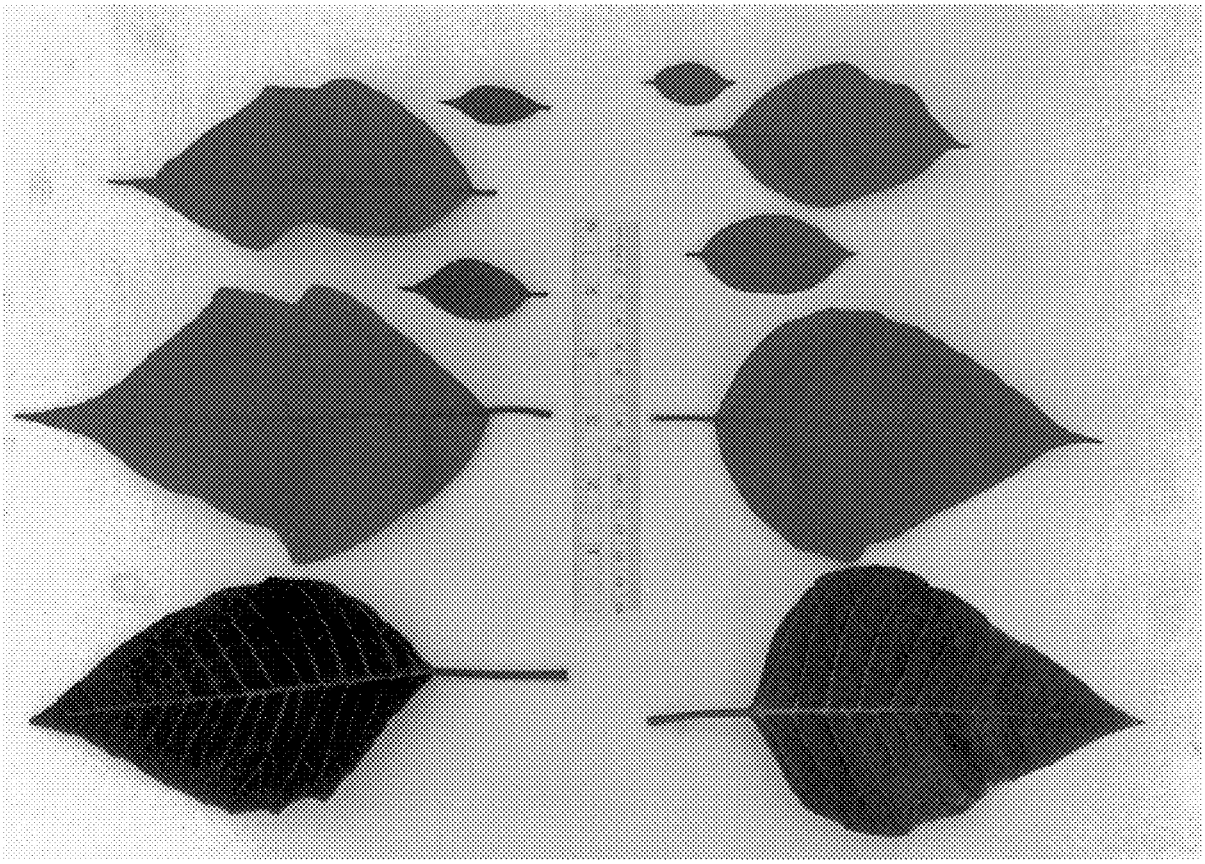

* * * * *